US00PP37706P2

(12) United States Plant Patent
Hoogendoorn

(10) Patent No.: US PP37,706 P2
(45) Date of Patent: Sep. 22, 2026

(54) ***HYDRANGEA* PLANT NAMED 'Perla57631'**

(50) Latin Name: *Hydrangea macrophylla*
Varietal Denomination: Perla57631

(71) Applicant: Cornelis Hoogendoorn, Zevenhuizen (NL)

(72) Inventor: Cornelis Hoogendoorn, Zevenhuizen (NL)

(73) Assignee: PERLANOVA BREEDING VOF, Zevenhuizen (NL)

( * ) Notice: Subject to any disclaimer, the term of this patent is extended or adjusted under 35 U.S.C. 154(b) by 0 days.

(21) Appl. No.: 19/414,233

(22) Filed: Dec. 9, 2025

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

U.S. PATENT DOCUMENTS

PP35,423 P2 * 10/2023 Hoogendoorn ..... Plt./250

* cited by examiner

*Primary Examiner* — Karen M Redden
(74) *Attorney, Agent, or Firm* — Penny J. Aguirre

(57) ABSTRACT

A new cultivar of *Hydrangea macrophylla* plant named 'Perla57631' that is characterized by its freely branched habit, its sturdy stems, its high resistance to warm and sunny weather conditions, and its inflorescences with sterile flower sepals that are bi-colored pink and white.

3 Drawing Sheets

Botanical classification: *Hydrangea macrophylla.*
Varietal denomination: 'Perla57631'.

BACKGROUND OF THE INVENTION

The present invention relates to a new and distinct cultivar of *Hydrangea macrophylla* and will be referred to hereafter by its cultivar name, 'Perla57631'. 'Perla57631' represents a new mophead type *Hydrangea*, a deciduous shrub grown for use as a landscape plant.

'Perla57631' was derived from an ongoing breeding program conducted by the Inventor in Zevenhuizen, The Netherlands. A goal of the breeding program is to develop new cultivars of *Hydrangea macrophylla* that are floriferous with bi-colored flowers, strong stems, and resistance to warm and sunny conditions.

The Inventor made a controlled cross in June of 2016 in Zevenhuizen, The Netherlands between unnamed and unpatented proprietary plants from the Inventor's breeding program; female parent (ref. code Perla1535361) and male parent (ref. code Perla1534425). 'Perla57631' was selected in June of 2019 as a single unique plant amongst the resulting seedlings.

Asexual propagation of the new cultivar was first accomplished under the direction of the Inventor by softwood stem cuttings in April of 2020 in Zevenhuizen, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Perla57631' as a unique cultivar of *Hydrangea.*

1. 'Perla57631' exhibits a freely branched habit.
2. 'Perla57631' exhibits sturdy stems.
3. 'Perla57631' exhibits a long blooming period.
4. 'Perla57631' exhibits high resistance to warm and sunny weather conditions.
5. 'Perla57631' exhibits inflorescences with sterile flower sepals that are bi-colored pink and white.

The female parent of 'Perla57631' differs from 'Perla57631' in having a taller plant height, less lateral branches, inflorescences that are more flattened in shape, and sterile flower sepals that are solid pink in color. The male parent of 'Perla57631' differs from 'Perla57631' in having a shorter plant height, a more densely branched habit with branches that are thinner and weaker, and inflorescences that are more globular in shape. 'Perla57631' can be most closely compared to the *Hydrangea macrophylla* cultivars 'Candy Heart' (not patented) and 'Tivoli' (not patented). Both 'Candy Heart' and 'Tivoli' are similar to 'Perla57631' in having sterile flower sepals that are bi-colored. 'Candy Heart' differs from 'Perla57631' in having a slightly denser branching habit with stems that are thinner and weaker, less resistance to sunny and warm weather conditions, and a shorter blooming period. 'Tivoli' differs from 'Perla57631' in having a less dense branching habit with stems that are thinner and weaker, less resistance to sunny and warm weather conditions, and a shorter blooming period.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Varb.

BRIEF DESCRIPTION OF THE DRAWINGS

The accompanying color photographs illustrates the overall appearance and distinct characteristics of the new *Hydrangea*. The photographs were taken of a 3-year-old plant as grown in a greenhouse in a 23-cm container in Zevenhuizen, The Netherlands.

The photograph in FIG. 1 provides a side view of the plant habit of 'Perla57631' in bloom.

Figure 1:
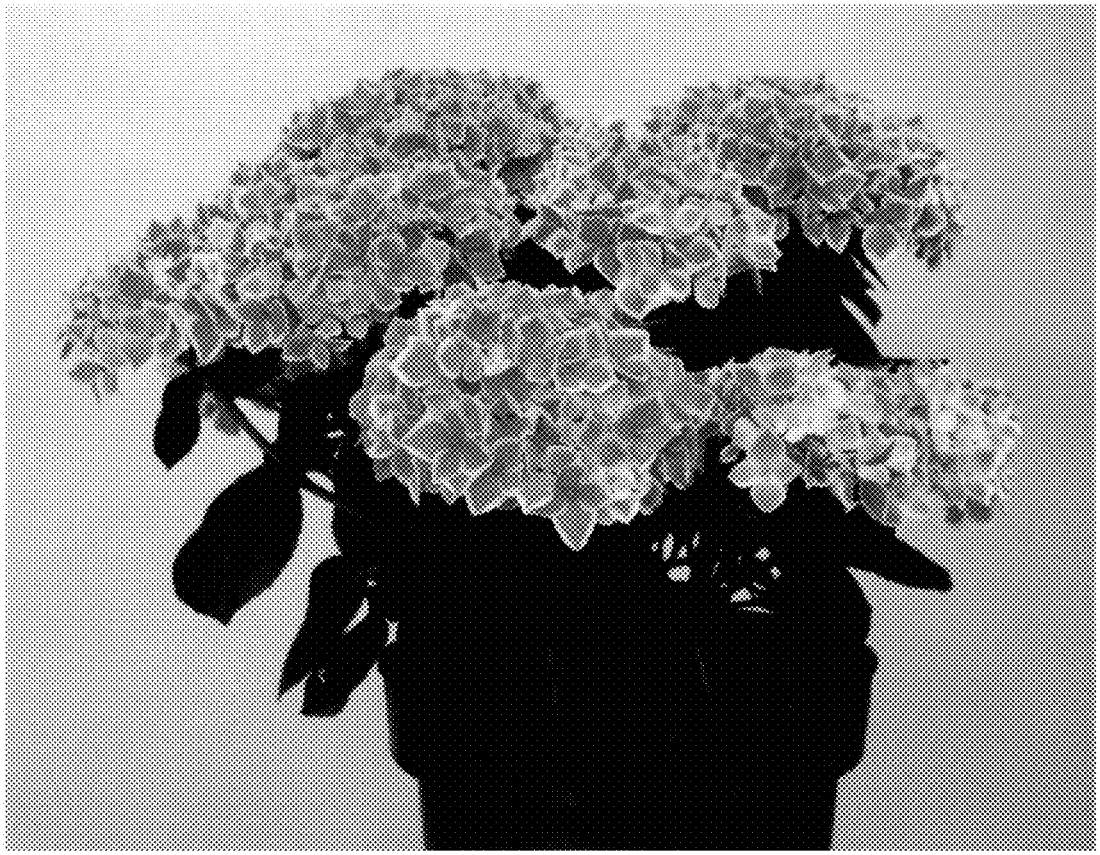
Figure 2:
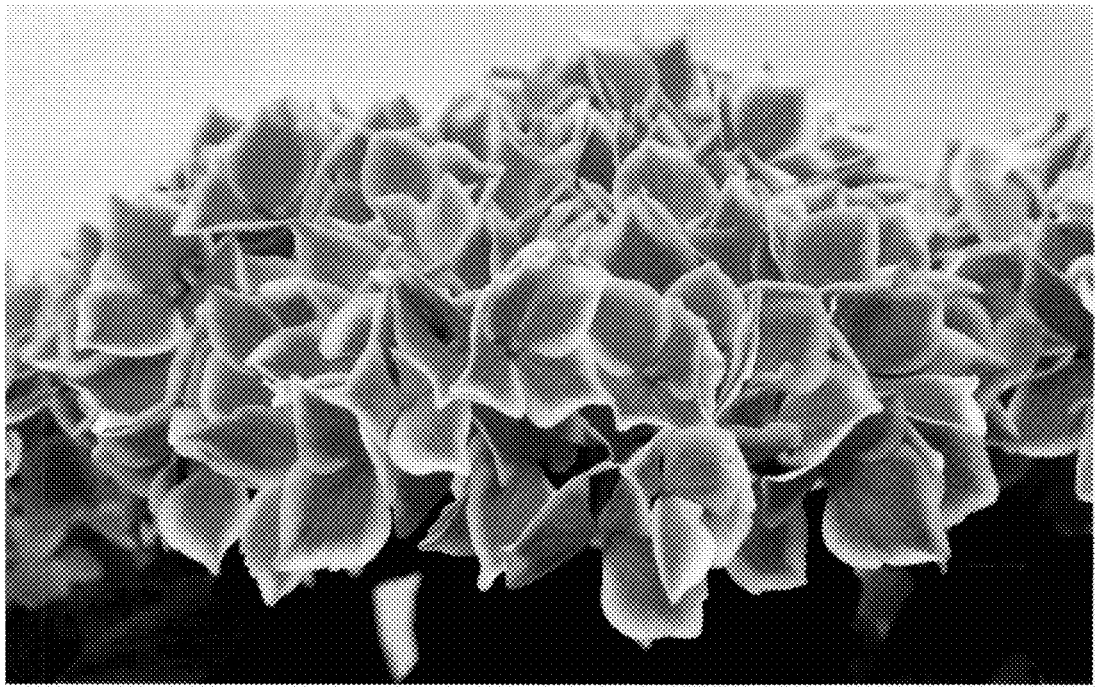

The photograph in FIG. 2 provides a close-up view of a mature inflorescence of 'Perla57631'.

Figure 3:
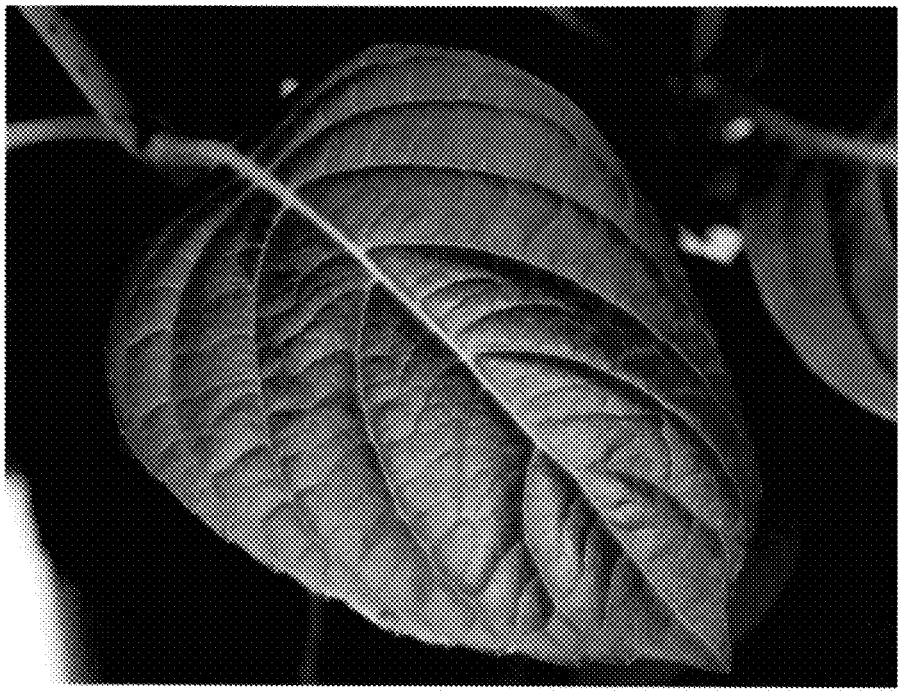

The photograph in FIG. 3 provides a close-up view of a leaf of 'Perla57631'.

Figure 4:
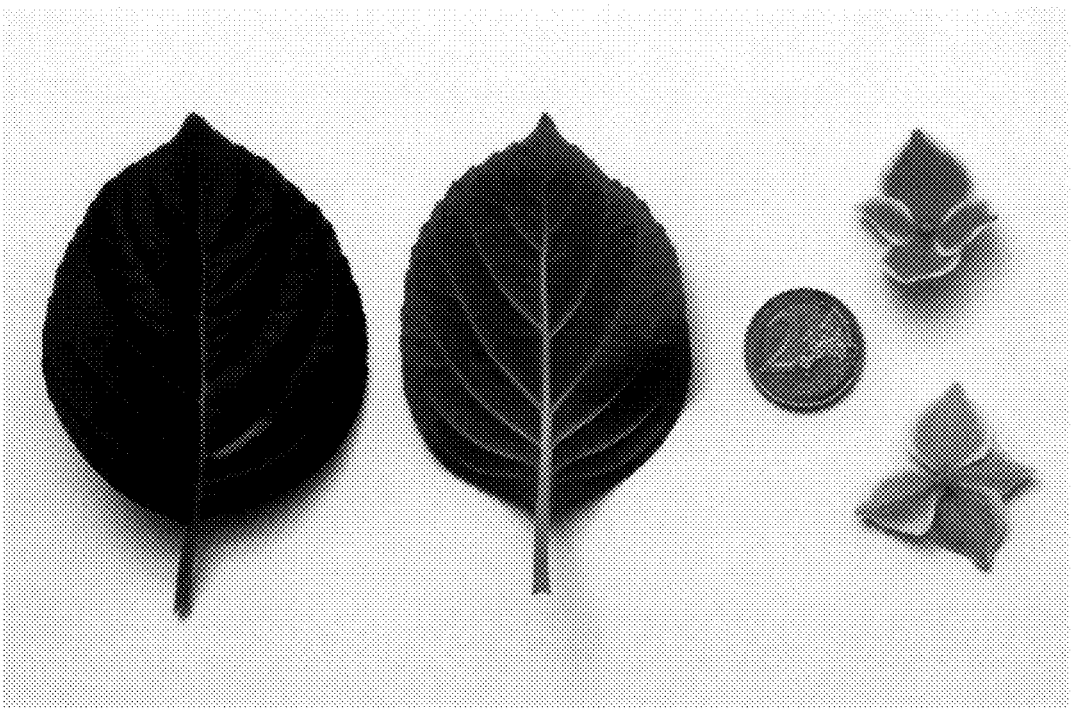

The photograph in FIG. 4 provides a view of the upper and lower surfaces of a leaf and the upper and lower surfaces of a sterile flower.

The colors in the photographs may differ slightly from the color values cited in the detailed botanical description, which accurately describe the colors of the new *Hydrangea*.

BOTANICAL DESCRIPTION OF THE PLANT

The following is a detailed description of 3-year-old plants of 'Perla57631' as grown in a greenhouse in 23-cm containers in Zevenhuizen, The Netherlands. The color determination is in accordance with the Sixth Edition 2015 (2019 reprint) Colour Chart of The Royal Horticultural Society, London, England, except where general color terms of ordinary dictionary significance are used.

General description:

*Blooming period*.—April to October in The Netherlands.

*Plant type*.—Deciduous shrub, mophead type *Hydrangea*.

*Plant habit*.—Broadly spreading, upright.

*Height and spread*.—Average of 55 cm in height, 50 cm in spread as grown in the landscape.

*Hardiness*.—At least in U.S.D.A. Zones 5 to 9.

*Diseases and pests*.—No resistance or susceptibility to diseases or pests has been observed.

*Root description*.—Fine and fibrous.

*Propagation*.—Softwood stem cuttings in spring and summer.

*Root development*.—Time required for root initiation is 4 to 5 weeks, time required to produce a young plant from rooted cutting is an average of 6 months.

Branch description:

*Branch shape*.—Rounded.

*Branch strength*.—Sturdy.

*Branch color*.—Young; 146D, mature; 144B, slightly tinged at the internodes with 183A, bark and older stems 199B to 199D and N199C and N199D.

*Branch size*.—An average of 12.2 cm in length, 5.5 mm in diameter.

*Branch surface*.—Younger and mature stems; glabrous, moderately covered with lenticels; oblong in shape, 2 mm in length, 0.5 mm in diameter, N186C in color.

*Branch aspect*.—Average angle of 60°.

*Internode length*.—Average of 5.9 cm.

*Branching*.—An average of 13 lateral branches per plant.

Foliage description:

*Leaf shape*.—Broadly elliptic to broadly oblong.

*Leaf arrangement*.—Opposite.

*Leaf division*.—Simple.

*Leaf base*.—Rounded.

*Leaf apex*.—Broadly apiculate.

*Leaf margins*.—Dentate-serrate.

*Leaf venation*.—Pinnate, upper and lower surface color; 146D.

*Leaf size*.—Average of 8.8 cm in length and 6.6 cm in width.

*Leaf attachment*.—Petiolate.

*Leaf surface*.—Both surfaces smooth and slightly rugose.

*Leaf color*.—Young upper surface NN137A, young lower surface; 146B, mature upper surface NN137A and 147A, mature lower surface; 147B.

*Petioles*.—An average of 1.9 cm in length and 4 mm in diameter, both surfaces slightly glossy and smooth, color; both surfaces 145A in color.

Inflorescence description:

*Inflorescence type*.—Terminal panicle, mophead in form, comprised of single sterile flowers and fertile flowers.

*Inflorescence shape*.—Flattened globular.

*Lastingness of inflorescence*.—Sterile flowers; 6 weeks, persistent, fertile flowers; 3 days, self-cleaning.

*Inflorescence number*.—One per lateral stem.

*Inflorescence size*.—Average of 10.3 cm in height, 14.7 cm in diameter.

*Flower number*.—Average of 300 sterile flowers and 45 fertile flowers per panicle.

*Flower fragrance*.—Faint sweet scent.

*Flower aspect*.—Sterile flowers; upright to outward, fertile flowers; upright.

*Flower size*.—Sterile flowers; an average of 3 cm in diameter, 1.1 cm in depth, fertile flowers; an average of 6 mm in diameter and 3 mm in depth.

*Flower type*.—Rotate.

*Flower buds*.—Sterile flowers; average of 9 mm in length, 1.8 cm in diameter, irregularly broadly cup-shaped, color; 150D, top 55C, fertile flowers; 3 mm in length and diameter, irregularly broadly cup-shaped, color; 84C, immature calyx 145B.

*Peduncles*.—Sturdy strength, average of 7 cm in length and 3.5 mm in width, color; 145A, distal end 195C, tinged N170C and N170D, held in a vertical angle, lateral peduncles 35° to main peduncle, surface is moderately covered with very short soft hairs, average of 0.3 mm, too small and too sparse to measure length or color.

*Pedicels*.—Sterile flowers; average of 1.4 cm in length and 1 mm in diameter, average angle of 25°, color; 70C, surface is matte and densely tomentose with very short hairs; average of 0.3 mm in length, too small to measure color, fertile flowers; average of 4 mm in length and 1 mm in diameter, average angle of 20°, color; 67B, surface is very slightly glossy, densely tomentose with short pubescence; 0.3 mm in length, too small to measure color.

*Petals*.—Sterile flowers; 4, rotate, cruciform in arrangement, 3 mm in length, 1.75 mm in diameter, ovate to concave in shape, acute apex, cuneate base, entire margins, glabrous, smooth, matte surface, color; when opening and fully open upper surface; N75A, when opening and fully open lower surface; 75A, fertile flowers; 4, rarely 5, rotate, 3 mm in length, 1.75 mm in diameter, ovate to concave in shape, acute apex, cuneate base, entire margins, glabrous and matte surface, color; when opening and fully open upper surface N75A, when opening and fully open lower surface 75A.

*Sepals*.—Sterile flowers; 3 or 4, occasionally 5, reniform to slightly to moderately carinate in shape, slightly to strongly overlapping, rotate, cruciform in arrangement, margins entire, occasionally 1 to 2 crenate teeth near the apex, apex is bluntly short apiculate, cuneate base, average of 1.9 cm in length and 1.6 cm in width, upper and lower surface glabrous and matte, color; when opening upper surface 63C, margins 155C, when opening lower surface 62C, margins 155C, when fully open upper surface 63B, margins NN155C, when fully open lower surface 63C, margins 155A, upper surface fading to 61B, margins 149C, lower surface fading to 70C, margins 152C to 152D, fertile flowers; 5, rotate in arrangement, broadly ovate in shape, entire margins, acute apex, cuneate base, average of 1 mm in length, 0.75 mm in width, both surfaces are glabrous and matte, color; when opening and fully open upper surface 145A, base 70C, when opening and fully open lower surface 145B.

Reproductive organs:

*Stamens*.—Sterile flowers; stamens; average of 8, anthers; broad oblong in shape, 2 mm in length and 75B in color, filaments; 2 mm in length, 75B in color, pollen; moderate to high in quantity, 155A in color, fertile flowers; stamens; average of 8, anthers; broadly oblong in shape, 0.8 mm in length and N77C in color, filaments; 2 mm in length and 75B in color, pollen; moderate to high in quantity and 155A in color.

*Pistils*.—Sterile flowers; pistils; 3, 2 mm in length, stigma; club-shaped, 1 mm in length and 75A in color, style; 70B in color, 1.5 mm in length, ovary; 70C in color, fertile flowers; pistils; 2 to 3, an average of 2 mm in length, stigma; club-shaped, 75A in color, style; 1.5 mm in length, 70B in color, ovary; 70C in color.

*Fruit and seed*.—Not observed to date.

It is claimed:

1. A new and distinct cultivar of *Hydrangea* plant named 'Perla57631' substantially as herein illustrated and described.

* * * * *